United States Patent [19]

Macek et al.

[11] Patent Number: 4,763,668
[45] Date of Patent: Aug. 16, 1988

[54] PARTIBLE FORCEPS INSTRUMENT FOR ENDOSCOPY

[75] Inventors: Andrew M. Macek; Mark W. Kozak, both of Euclid; Edward J. Smith, Hinckley, all of Ohio

[73] Assignee: Mill Rose Laboratories, Mentor, Ohio

[21] Appl. No.: 792,093

[22] Filed: Oct. 28, 1985

[51] Int. Cl.⁴ .............................................. A61B 17/32
[52] U.S. Cl. ..................................... 128/751; 128/321
[58] Field of Search ............... 128/305, 310, 321, 751, 128/346

[56] References Cited

U.S. PATENT DOCUMENTS

| | | | |
|---|---|---|---|
| 2,034,785 | 3/1936 | Wappler | 128/321 |
| 3,895,636 | 7/1975 | Schmidt | 128/305 |
| 3,958,576 | 5/1976 | Komiya | 128/346 |
| 3,964,468 | 6/1976 | Schulz | 128/305 |
| 4,010,737 | 3/1977 | Vilaghy et al. | 128/310 |
| 4,038,987 | 8/1977 | Komiya | 128/321 |
| 4,467,802 | 8/1984 | Maslanka | 128/321 |
| 4,646,751 | 3/1987 | Maslanka | 128/321 |

OTHER PUBLICATIONS

Olympus; Jun. 1982.
Davol Biopsy Forcep.
Western Surgical Specialties; Dec. 1984.
Micro Vasive Challenger Biopsy Forceps; Jul. 1985.
Olympus Catalog; Olympus Corporation; 1984; p. 11.

Primary Examiner—C. Fred Rosenbaum
Assistant Examiner—H. Macey
Attorney, Agent, or Firm—Watts, Hoffmann, Fisher & Heinke Co.

[57] ABSTRACT

A partible forceps instrument for endoscopy separable into an operating segment and a sampling segment and having a cleaning fixture.

26 Claims, 2 Drawing Sheets

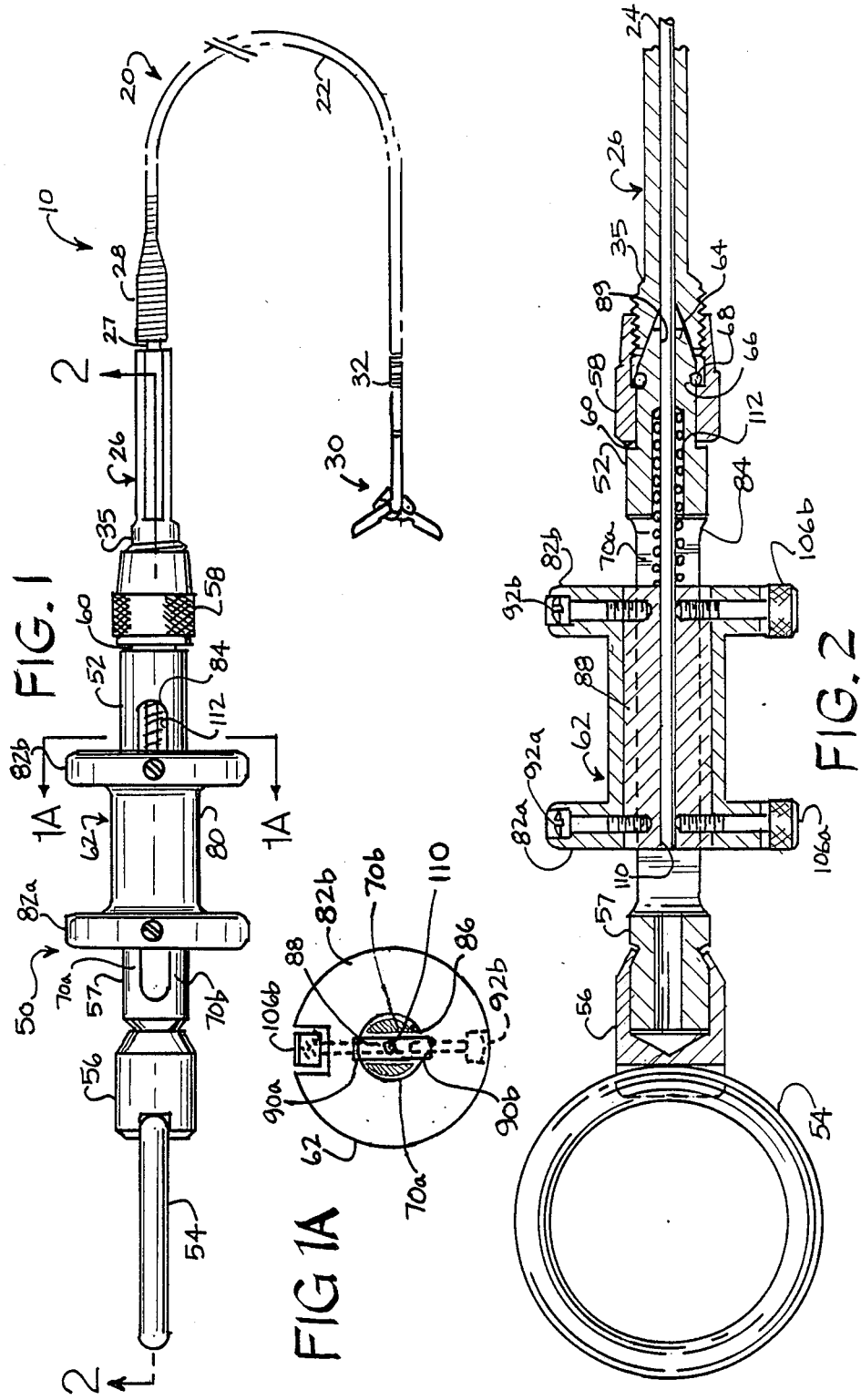

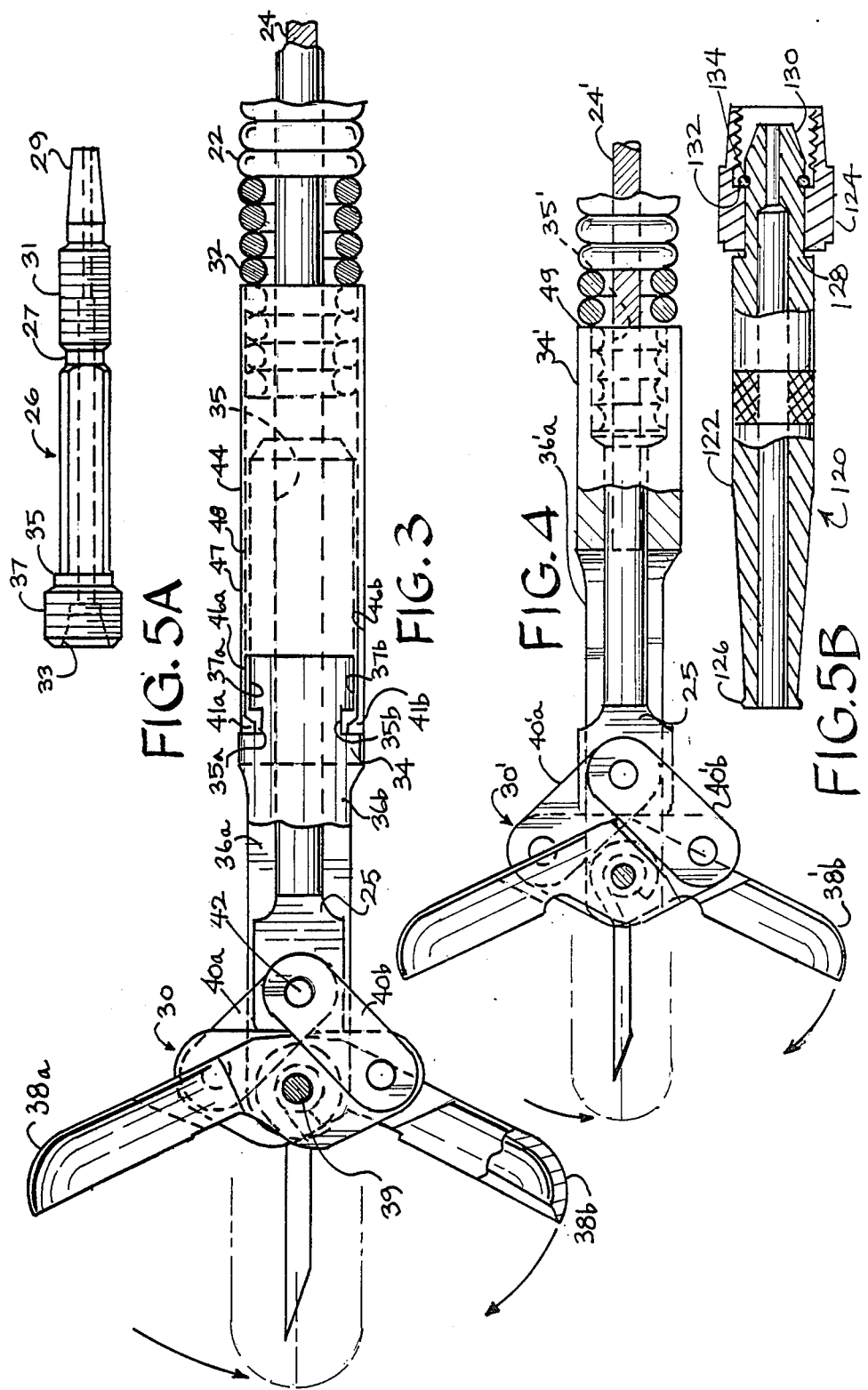

4,763,668

PARTIBLE FORCEPS INSTRUMENT FOR ENDOSCOPY

DESCRIPTION

1. Technical Field

This invention relates generally to flexible forceps instruments for endoscopy and, more particularly, to a partible forceps instrument.

2. Background Art

Flexible forceps instruments for endoscopic use, such as gastroscopy, bronchoscopy and the like, typically are constructed as an inseparable instrument having a cable with forceps pincers welded to one end and a spring mounted operating handle welded to the other end. The cable is enclosed within a flexible, coiled sheath that is permanently attached to the operating handle at one end and to the base of the forceps pincers at the other end. Pushing the cable forward relative to the sheath by means of the handle causes the pincers to open.

Some of the advantages of inseparable forceps instruments are that they are difficult to clean after use and that they are difficult to repair when damaged.

During use, the interior of the forceps, the cable and the sheath become soiled. The delicate forceps become clogged with material which is difficult to dislodge. Even subjecting the instrument to ultrasonic cleaning will not thoroughly clean the operating cable and sheath in as much as the ultrasound dislodges particulate matter but does not flush it out of the sheath. Thus, the dislodged matter may dry and block the cable or the forceps.

The forceps instrument may be damaged in use when the operator attempts to force the flexible cable and sheath through an endoscope with the result that the coiled sheath develops a kink which inhibits or impairs the relative movement of the cable. The instrument may also be damaged when the operator applies too much tension on the cable in an attempt to close the forceps on a specimen. Since the base of the forceps is mounted to the sheath, too much tension on the cable can rupture the weld between the cable and the forceps pincer mechanism. Typically, repair involves returning the instrument to the manufacturer for rebuilding. The advantage of inseparable forceps instruments is the stability and handling afforded by unitary construction.

DISCLOSURE OF THE INVENTION

The present invention provides a partible forceps instrument for endoscopy which has the stability and handling of conventional inseparable forceps and which has separable parts and a cleaning fixture to provide for complete cleaning and flushing of the instrument. The separability allows for replacement or interchangeability of parts and permits for a smaller inventory of forceps parts.

More particularly, the invention is a flexible forceps instrument comprising a cable sheath, a forceps having a scissor mechanism demountably attached to a distal end of the sheath, a connector attached to a proximal end of the sheath, a manual operating assembly demountably attached to the connector and an operating cable inside the sheath attached at a distal end to the scissor mechanism of the forceps and demountably attached at a proximal end to the manual operating assembly. The present invention also provides for a flexible forceps instrument system which includes a cleaning fixture attachable to the sampling segment in place of the manual operating assembly. The fixture is in the form of a hollow tube having an inlet at one end for receiving cleaning fluid under pressure and having a coupler at the other end or outlet end to attach the fixture to the connector of the sampling segment.

The invention further provides for a sampling segment having a connector whereby the sampling segment is useable with the manual operating assembly for endoscopic use or is placed in condition for cleaning after use by attachment to the cleaning fixture.

One advantage of the construction of the present invention is that the biopsy instrument may be disassembled to facilitate cleaning the interior of the sheath and the cable.

Another advantage of the present invention is that a cleaning fixture is provided to facilitate the introduction of cleaning fluid under pressure into the interior of the sheath to flush out trapped particulate matter.

Yet another advantage of the present invention is that a sampling segment is provided which allows various lengths of sheath enclosed cable and various forceps designs to be used interchangeably with the same manual operating assembly.

A further advantage of the present invention is that the sampling segment allows for replacement or repair of damaged sheaths or damaged forceps without the need for replacing or repairing the entire instrument.

Other advantages and a more complete understanding of the invention will be had from the following detailed description when taken in conjunction with the accompanying drawings.

BRIEF DESCRIPTION OF THE DRAWINGS

FIG. 1 is a partial plan view of the flexible biopsy instrument;

FIG. 1A is a cross-sectional view of FIG. 1 taken along the line 1A—1A of FIG. 1;

FIG. 2 is a partial longitudinal-sectional view of FIG. 1 taken along the line 2—2 of FIG. 1;

FIG. 3 is a partial cross-sectional view of a demountable forceps of the flexible biopsy instrument;

FIG. 4 is a partial cross-sectional view of a unitary forceps and sheath of the flexible biopsy instrument;

FIG. 5A is a side view of the connector of the biopsy instrument; and

FIG. 5B is a side view partially in section of the cleaning fixture.

BEST MODE FOR CARRYING OUT THE INVENTION

Referring to FIGS. 1-2, the flexible forceps instrument, shown generally at 10, has a sampling segment 20 and a operating segment 50.

The sampling segment 20 is composed of a coiled spring sheath 22, an operating cable 24 within the sheath 22, a connector 26 attached to the proximal end 28 of the sheath 22, and a sampling forceps 30 attached to the distal end 32 of the sheath 22.

As shown in FIG. 3, the sampling forceps 30 has a pincer supporting body 34 with a passage 35 through which the operating cable 24 passes. Two laterally spaced prongs 36a, 36b extend distally from the body 34 between which pincers 38a, 38b are mounted on a fixed pivot shaft 39. Pincer operating links 40a, 40b pivotally connect the distal end 25 of the operating cable 24 to the pincers. The operating cable 24 is connected to the pincer operating links through a pivot 42. A similar forceps 30' is shown in FIG. 4, in which like parts are designated by the same reference numeral as in the forceps 30, but with a prime designation.

The sampling forceps 30 as shown in FIGS. 3 and 4 are of the biopsy cup type with needle. It is to be understood that many types of forceps such as, but not limited to, biopsy forceps, grasping forceps, or scissors may be employed.

In the preferred embodiment shown in FIG. 3, the sheath 22 is demountably mounted on the body 34 of the sampler forceps 30. A sheath collar 44 is attached to the distal end 32 of the sheath 22. The sheath collar 44 has a pair of distally projecting fingers 46a, 46b extending from diametrically opposite sides of the collar 44. The width of each finger is approximately one-half the diameter of the collar 44. Each finger has a base portion, as at 47, formed by a pair of slits in the collar, as at 48, extending proximally into the collar 44. This construction and the spring steel of which the collar is formed impart spring-like resiliency to the fingers. Each of the fingers 46a, 46b is provided with an inwardly facing tooth 41a, 41b. The teeth 41a, 41b snap into and out of a pair of corresponding oppositely facing flat grooves 35a, 35b in a pair of oppositely facing mounting portions 37a, 37b of the body 34 of the sampler forceps 30. The mounting portions 37a, 37b are in the form of flat external surfaces against which the fingers abut and which effectively reduce the diameter of the body 34 to allow the collar 44 to be snapped onto the body 34 via the projections 46a, 46b and the teeth 41a, 41b without presenting an increased diameter periphery. In another embodiment as shown in FIG. 4, the sheath 22' is non-demountably attached to the body 34' of the sampler forceps 30' by a friction closure 49 or the like.

As shown in FIGS. 1 and 5A, the connector 26 has a reduced diameter distal portion 27 with a tapered end which the proximal end 28 of the sheath 22 is threaded and then permanently attached by welding or the like. The adapter 26 has an increased diameter proximal end 35 with external threads 37 and an internal conical surface 33.

The operating segment 50, as best shown in FIGS. 1 and 2, has a central shaft 52, a cable slide 62 slidably mounted on the shaft 52, a thumb ring 54 with a connecting collar 56 crimped to be freely rotatable on a proximal end 57 of the shaft 52, and an internally threaded coupler nut 58 freely rotatably about a reduced diameter distal portion 60 of the shaft 52. As best seen in FIG. 2, the reduced diameter distal portion 60 of the shaft 52 has a tapered portion 64 and a snap-ring groove 66. The snap-ring groove 66 receives a snap-ring 68 which mounts the coupler nut 58 on the reduced diameter distal portion 60 of the shaft 52. The coupler nut 58 serves to demountably attach the sampler segment 20 to the operating segment 50. The tapered portion 64 of the shaft 52 engages the internal conical surface 33 of the increased diameter proximal portion 35 of the connector 26 and provides a stable connection that resists deformation or flexion during manipulation of the instrument.

The cable slide 62 is in the form of a spool to facilitate gripping between the index and third finger of the operator's hand. The slide 62 has a central portion 80 and increased diameter flanges 82a, 82b to define the spool shape. The central shaft 52 has an elongated lateral passage 84 which forms a pair of tracks 70a, 70b, extending substantially the length of the shaft 52, upon which the cable slide 62 is slidably mounted. The elongated lateral passage 84 communicates with a reduced diameter passage 89 extending longitudinally through the distal portion 60 of the shaft 52 that receives the operating cable 24.

As best seen in FIG. 1A, the cable slide 62 has a throughbore 86 to accommodate the tracks 70a, 70b. Rotation of the slide 62 about the central shaft 52 is prevented by means of a core member 88 which is located in longitudinal recesses 90a, 90b in throughbore 86. A pair of counter-sunk set screws 92a, 92b within the flanges 82a, 82b retains the core member 88 within the slide 62.

The operating cable 24 is demountably attached to the slide 62 by means of a pair of thumb screws 106a, 106b which fasten the cable 24 in a bore 110 of the core member 88 at longitudinally spaced locations.

A compression spring 112 is interposed between the slide 62 and the distal end of the lateral passage 84 around the operating cable 24. The spring 112 biases the slide 62 and the operating cable 24 to a position in which the forceps 30 are closed. An operator moving the slide 62 so as to compress the spring 112 causes the operating cable 24 to move distally toward the fixed pivot shaft 39 to cause the pincers 38a, 38b to open in order to take a biopsy sample. When the operator is satisfied the pincers are properly located to take a sample, the slide 62 is released from the index and third finger and the expansion of the spring 112 moves the slide 62 and operating cable 24 proximally to cause the pincers 38a, 38b to close.

After the instrument has been used to take a biopsy specimen, the instrument is prepared for cleaning and re-use by disassembly into the sampler segment 20 and the operating segment 50. The thumb screws 92a, 92b in the cable slide 62 are loosened to release the operating cable 24 from the bore 110 of the core member 88. The coupler nut 58 is rotated to free the operating segment 50 from the sampling segment 20. If the body 34 to which the operating cable 24 is attached is demountably mounted on the sheath 22 as shown in FIG. 3, the body and cable are removed by unsnapping the teeth 41a, 41b of the fingers 46a, 46b of the sheath collar 44 from the flat grooves 35a, 35b in the body 34 of the sampler forceps 30 and the cable pulled out of the sheath 22 from the distal end. If the operating cable 24 is non-demountably attached to the sheath 22, as with the body 34' shown in FIG. 4, no further disassembly prior to cleaning is possible.

A cleaning fixture 120, as shown in FIG. 5B, facilitates cleaning the operating segment 20 and comprises a hollow tube 122 having an internally threaded coupler 124 at one end and an inlet 126 at an other end to receive a source of cleaning fluid under pressusre, such as from a syringe. The inlet end 126 may be in the form of a luer lock or the like. The coupler 124 is freely rotatable about a reduced diameter portion 128 of the tube 122. The reduced diameter portion 128 has tapered portion 130 and a snap-ring groove groove 132 which receives a snap-ring 134. The snap-ring 134 retains the coupler 124 on the reduced diameter portion 128 of the tube 122. The coupler 124 of the cleaning fixture 120 is substantially identical to the coupler nut 58 of the operating segment 50, so that the cleaning fixture 120 may be interchanged with the operating segment 50. For cleaning the sampling segment 20, the coupler 124 of the cleaning fixture 120 is attached to the externally threaded increased diameter portion of the connector 26. The tapered portion 130 of the cleaning fixture 120 engages the internal conical surface 33 of the connector 26 and provides a fluid tight connection for introducing cleaning fluid into the interior of the connector 26 and sheath 22. Cleaning fluid may be introduced under pressure with a syringe having a luer lock coupleable to the inlet 126. This fixture is especially advantageous when the cable cannot be removed from the sheath because it is otherwise difficult to flow fluid through the sheath. The present invention thus provides a system in which a separable or partible forceps and a cleanianag fixture cooperate to provide the advantages set forth.

Variations and modifications of the invention will be apparent to those skilled in the art from the above detailed description. Therefore, it is to be understood that, within the scope of the appended claims, the invention can be practiced otherwise than as specifically shown and described.

We claim:

1. A flexible biopsy instrument comprising:
    a cable sheath having forceps-attaching means including a resilient member attached to the distal end of said cable sheath;
    a forceps having a scissor mechanism and receiving means demountably engaged by said forceps attaching means, said receiving means including a recess for receiving said resilient member, said forceps demountably attached to a distal end of said cable sheath;
    a connector attached to a proximal end of said cable sheath;
    a manual operating assembly including scissor mechanism actuating means demountably attached to said connector; and
    an operating cable within said sheath and said connector attached at a distal end to said scissor mechanism of said forceps and demountably attached at a proximal end to said scissor mechanism actuating means.

2. A flexible biopsy instrument as claimed in Claim 1 wherein said forceps-attaching means further includes a collar attached to said distal end of said sheath, said collar supporting said resilient member, and said receiving means of said forceps further includes a forceps pincer supporting body slidably receivable in said collar, said body having a mounting portion for receiving said resilient member.

3. A flexible biopsy intrument as claimed in claim 2 wherein said resilient member comprises a finger having a locking tooth and said mounting portion includes a recess for receiving said locking tooth.

4. A flexible biopsy instrument as claimed in claim 3 wherein said mounting portion further includes a flat abutment surface for abutting engagment with said finger.

5. A flexible biopsy instrument as claimed in claim 1 wherein said connector comprises a hollow tube having a coupling means at one end for demountably coupling said connector to said manual operating assembly and further having a cable sheath attachment portion at another end for attaching said cable sheath to said connector.

6. A flexible biopsy instrument as claimed in claim 1 wherein said manual operating assembly includes:
    a central shaft having a throughbore for receiving said operating cable;
    a coupling nut rotatably mounted on a distal end of said shaft, said coupling nut adapted to couple with said connector; and
    a cable slide slidably mounted on said central shaft, said cable slide having means for releaseably receiving said operating cable.

7. A flexible biopsy instrument as claimed in claim 6 wherein said manual operating assembly further includes a thumb-ring rotatably mounted on a proximal end of said central shaft.

8. A flexible biopsy instrument system comprising:
    a sampling segment including:
    a cable sheath, a forceps having a scissor mechanism, said forceps attached to a proximal end of said cable sheath, and an operating cable within said sheath and said connector attached at a distal end to said scissor mechanism of said forceps;
    an operating segment including:
    a manual operating assembly including scissor mechanism actuating means, means for demountably connecting said manual operating assembly to said connector, and means for demountably connecting said operating cable to said scissor mechanism actuating means; and
    a cleaning fixture including:
    a hollow tube having an inlet at one end to receive fluid under pressure and having connecting means at another end for demountably connecting said fixture to said connector in place of said manual operating assembly.

9. A flexible biopsy instrument as claimed in claim 14 wherein said forceps are demountably attached to said distal end of said cable sheath.

10. A flexible biopsy instrument system as claimed in claim 9 wherein said cable sheath has forceps-attaching means for demountably attaching said forceps to a distal end of said sheath and wherein said forceps has receiving means engaged by said forceps-attaching means.

11. A flexible biopsy instrument system as claimed in claim 10 wherein said forceps attaching means includes a resilient member attached to said distal end of said sheath, and said receiving means of the forceps includes a recess for receiving the resilient member.

12. A flexible biopsy instrument system as claimed in claim 10 wherein said forceps-attaching means includes a collar attached to said distal end of said sheath, said collar having a resilient member, and said receiving means of said forceps includes a forceps pincer supporting body slidably receivable in said collar, said body having a mounting portion for receiving said resilient member.

13. A flexible biopsy instrument system as claimed in claim 12 wherein said resilient member comprises a finger having a locking tooth and said mounting portion includes a recess for receiving said locking tooth.

14. A flexible biopsy instrument system as claimed in claim 13 wherein said mounting portion further includes a flat abutment surface for abutting engagement with said finger.

15. A flexible biopsy instrument system as claimed in claim 8 wherein said connector comprises a hollow tube having a coupling means at one end for demountably coupling said connector to said manual operating assembly and further having a cable sheath attachment portion at another end for attaching said cable sheath to said connector.

16. A flexible biopsy instrument system as claimed in claim 8 wherein said manual operating assembly includes:
    a central shaft having a throughbore for receiving said operating cable;

a coupling nut rotatably mounted on a distal end of said shaft, said coupling nut adapted to couple with said connector; and a cable slide slidably mounted on said central shaft, said cable slide having means for releasably receiving said operating cable.

17. A flexible biopsy instrument system as claimed in claim 16 wherein said manual operating assembly further includes a thumb-ring rotatably mounted on a proximal end of said central shaft.

18. A sampling segment for endoscopic use comprising:

a cable sheath forceps-attaching means including a resilient member attached to the distal end of said cable sheath;

a forceps having a scissor mechanism and receiving means demountably engaged by said forceps attaching means, said receiving means including a recess for receiving said resilient member, said forceps demountably attached to a distal end of said cable sheath;

a connector attached to a proximal end of said cable sheath;

an operating cable within said sheath and said connector attached at a distal end to said scissor mechanism;

said connector having coupling means on a proximal end whereby said sampling segment is coupleable with a manual operating assembly having a scissor mechanism actuating means attachable to the proximal end of the operating cable for use in endoscopic procedures or whereby said sampling segment is coupleable with a cleaning fixture for introducing cleaning fluid under pressure into the interior of said sampling segment.

19. A sampling segment as claimed in claim 18 wherein said forceps-attaching means further includes a collar attached to said distal end of said sheath, said collar supporting said resilient member, and said receiving means of said forceps further includes a forceps pincer supporting body slidably receivable in said collar, said body having a mounting portion for receiving said resilient member.

20. A sampling segment as claimed in claim 19 wherein said resilient member comprises a finger having a locking tooth and said mounting portion includes a recess for receiving said locking portion includes a recess for receiving said locking tooth.

21. A sampling segment as claimed in claim 20 wherein said mounting portion further includes a flat abutment surface for abutting engagement with said finger.

22. A sampling segment as claimed in claim 18 wherein said connector comprises a hollow tube.

23. A flexible biopsy instrument comprising:

a cable sheath having a collar at a distal end, said collar including a resilient finger having a locking tooth;

a forceps having a scissor mechanism, said forceps demountably attached to the distal end of said sheath, said forceps including a forceps pincer supporting body slidably receivable in said collar, said body having a mounting portion for receiving said resilient finger, said mounting portion including a recess for receiving said locking tooth and further including a flat abutment surface for abutting engagement with said finger;

a connector attached to a proximal end of said cable sheath;

a manual operating assembly including scissor mechanism actuating means demountably attached to said connector; and an operating cable within said sheath and said connector attached to a distal end to said scissor mechanism of said forceps and demountably attached at a proximal end to said scissor mechanism actuating means.

24. A flexible biopsy instrument comprising:

a cable sheath having a proximal and a distal end;

a cable operator attached to the proximal end of the sheath;

a forceps unit having as connected parts, a body, forceps-pincers pivotably connected to the body and a cable connected to the forceps-pincers;

means on the forceps unit and the distal end of the cable sheath cooperable to demountably attach the forceps unit to the sheath; and means on the cable operator for releasably securing the forceps unit whereby the forceps unit can be removed from the sheath and cable operator without disassembly of the unit parts.

25. The biopsy instrument of claim 24 wherein one of the means on the forceps unit and the distal end of the cable sheath comprises a collar that releasably receives the other means to form a forceps-unit-to-sheath coupling.

26. The biopsy instrument of claim 25 wherein the means on the forceps unit and the distal end of the cable sheath are constructed and arranged so that when the collar releasably receives the other means, the peripheral diameter of the forceps-unit-to-sheath coupling on the cable sheath is essentially equal to the peripheral diameter of the coupling on the forceps-unit.

* * * * *